Dec. 12, 1972 C. G. KLEHM Plant Pat. 3,268
PEONY PLANT
Filed Feb. 18, 1971
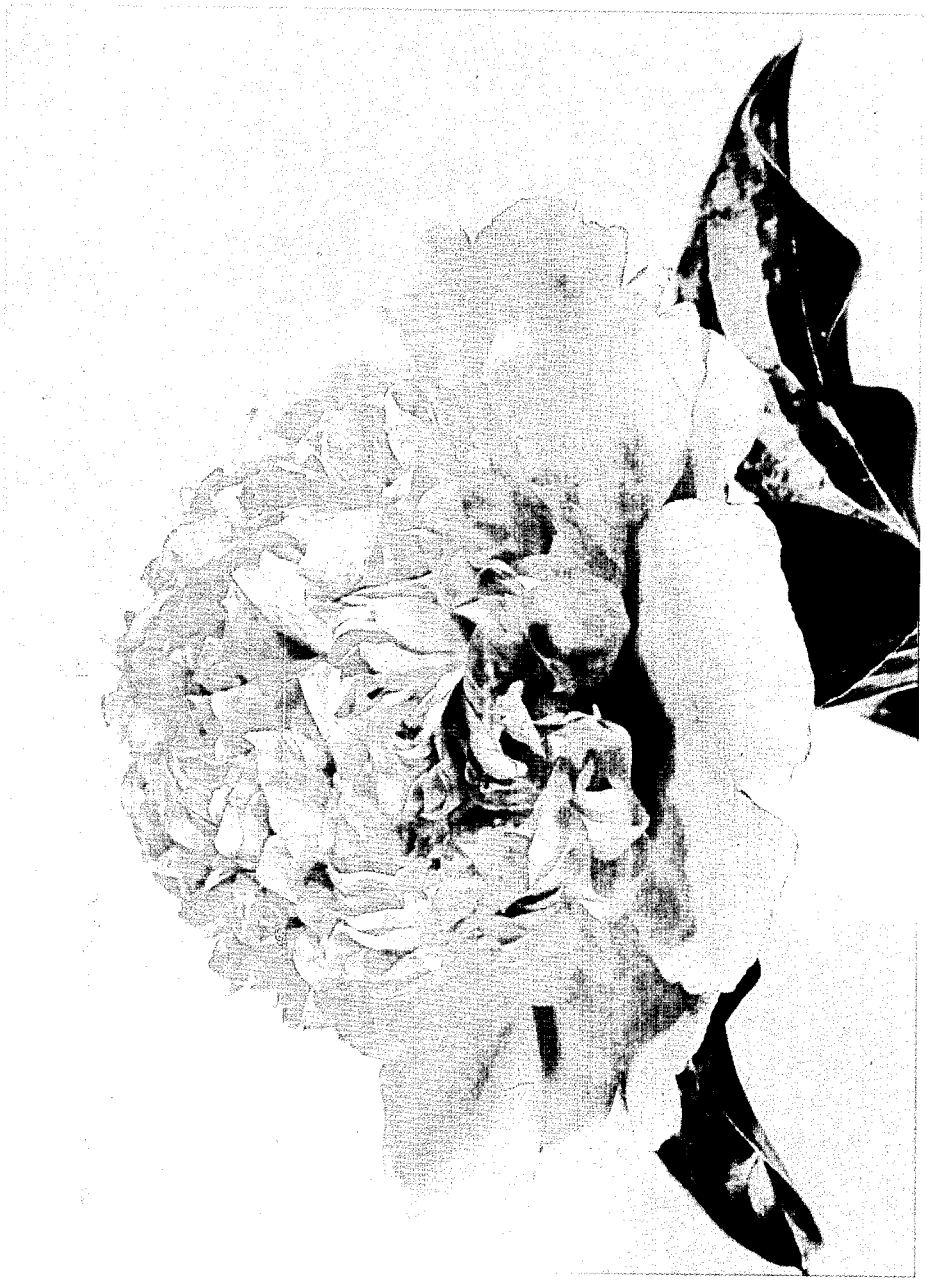
Inventor.
Carl G. Klehm
By: Robb & Robb
Attorneys.

United States Patent Office

Plant Pat. 3,268
Patented Dec. 12, 1972

3,268
PEONY PLANT

Carl G. Klehm, 2 E. Algonquin Road,
Arlington Heights, Ill. 60005

Filed Feb. 18, 1971, Ser. No. 116,687
Int. Cl. A01h 5/00
U.S. Cl. Plt.—68 1 Claim The present invention relates to a new and distinct variety of peony plant of the species botanically known as *Paeonia lactiflora,* which was originated by me by crossing an unnamed and unpatented "bull" type peony seedling, identified in my breeding records as No. 71D, with the peony variety known as "Mons. Jules Elie" (unpatented), the unnamed seedling being the male parent and being an $F_1$ seedling of "Mons. Jules Elie," and "Mons. Jules Elie" being the female parent.

My new variety resulted from an extensive and prolonged program of breeding and testing conducted by me in an effort to produce new and improved or unique peony variations, and was selected as one of many outstanding varieties resulting from this breeding program because of its unique combination of the following principal characteristics which distinguish the new variety from its parents, as well as from all other peony varieties of which I am aware:

(1) A vigorous and strong plant habit;
(2) Exceptionally thick, stout and strong stems;
(3) Large, thick and clean foliage;
(4) Extremely large, many-petalled and high-crowned flowers of a fully double-rose type form and the petals of which unfold with a "crater" effect of seemingly unending ruffled petals;
(5) A distinctive and attractive light red flower color; and
(6) Especial suitability for garden and landscape use, including border or background uses for other flower settings, as well as for cut-flower use.

Asexual reproduction of my new peony variety by root division, as performed by me in my nursery located at Arlington Heights, Illinois, shows that the foregoing characteristics and distinctions come true to form and are established and transmitted through succeeding propagations.

The accompanying drawing shows typical specimens of the vegetative growth and flowers of my new variety, as depicted in color as nearly true as it is reasonably possible to make the same in a color illustration of this character.

The following is a detailed description of the new variety, with color terminology in accordance with the Horticultural Colour Chart (1966 Edition), published by The Royal Horticultural Society, of London, England, as based on specimens grown and observed by me at Arlington Heights and Barrington, Ill.:

Breeding: Seedling.
*Pollen parent.*—An unnamed $F_1$ seedling of "Mons. Jules Elie" identified as No. 71D.
*Seed parent.*—"Mons. Jules Elie."
Propagation: Holds its distinguishing characteristics through succeeding propagations by root division.

*Flower*

Blooming habit: Annual.
Blooming season: Considered as a late season bloomer.
Bud:
*Size.*—Extremely large.
*Form.*—Slightly ribbed, but basically round.
*Color.*—Currant Red, Fan 1, Plate 46 A'.
*Sepals.*—Uneven edges. Color—Smooth green.
*Calyx.*—Polysepalous.
*Opening.*—Opens easily and dependably, with occasional splitting.

Bloom:
*Size.*—Large and high (about 8 inches to 8½ inches wide and about 4½ inches to 5 inches high).
*Borne.*—Singly; one main bud per stem, with from 2 to 4 auxiliary buds.
*Stems.*—Thick (up to ⅝ inch in diameter at base; believed to be the thickest stems of all *P. lactiflora* varieties.
*Form.*—Double-rose type and high crowned.
*Petalage.*—Extremely double.
*Color.*—Light red correspond to Guardsman Red, Fan 1, Plate 45 A'.
*Variegations.*—None.
*Discolorations.*—None.
Petals: Many more petals than either parent.
*Texture.*—Thick.
*Appearance.*—Fluffy.
*Form.*—Recurved; slightly notched.
*Arrangement.*—Imbricated.
*Persistence.*—Above average.
*Fragrance.*—Strong peony fragrance.
*Lasting qualities.*—Excellent.
Reproductive organs:—None.

*Plant*

Form: Bush.
Growth: Outstanding strength.
Foliage:
*Leaflets.*—From 5 to 7 in number.
*Size.*—Large.
*Quantity.*—Above average.
*Color.*—Clean almond green, Fan 3, Plate 136 B'.
*Shape.*—Elliptically acute.
*Texture.*—Pronounced veins.
*Edge.*—Smooth.
*Serrations.*—None.
*Leaf stem.*—Thick; strong.
*Stipules.*—None.
*Disease resistance.*—Resistant to leaf blotch and other bacterial peony diseases, as determined by comparison with other varieties for many years as grown at Arlington Heights and Barrington, Illinois.

*General observations*

The new variety shows every sign of polyploidy conditions, with extremely thick stems, larger and thicker foliage than in either parent, larger and many more petalled and high-crowned flowers than in either parent, combined with a commendable plant habit of excellent vigor and strength. The flowers have an unusual petal unfolding habit which gives a "crater" effect of seemingly unending ruffled petals as the petals unfold off the center meristem. The light red color of the flowers is seldom seen in the *P. lactiflora* species.

I claim:

1. A new and distinct variety of peony plant of the species botanically known as *Paeonia lactiflora,* substantially as herein shown and described, characterized particularly as to novelty by the unique combination of a vigorous and strong plant habit, exceptionally thick, stout and strong stems, large, thick and clean foliage, extremely large, many-petalled and high-crowned flowers of a fully double-rose type form and the petals of which unfold with a "crater" effect of seemingly unending ruffled petals, a distinctive and attractive light red flower color, and especial suitability for garden and landscape use, including border or background uses for other flower settings, as well as for cut-flower use.

No references cited.

ROBERT E. BAGWILL, Primary Examiner